United States Patent [19]
Grabowski

[11] Patent Number: 5,956,968
[45] Date of Patent: Sep. 28, 1999

[54] COLD PACK FOR VIALS CONTAINING MEDICINE

[75] Inventor: Paul P. Grabowski, Portage, Mich.

[73] Assignee: Pharmacia & Upjohn Company, Kalamazoo, Mich.

[21] Appl. No.: 08/934,416

[22] Filed: Sep. 19, 1997

Related U.S. Application Data

[60] Provisional application No. 60/026,565, Sep. 23, 1996.

[51] Int. Cl.⁶ ...................................................... F25D 3/14
[52] U.S. Cl. .......................................... 62/457.2; 220/500
[58] Field of Search ................................ 62/457.1, 457.2, 62/529, 530; 220/500; 206/438, 538, 570

[56] References Cited

U.S. PATENT DOCUMENTS

| | | | |
|---|---|---|---|
| 4,393,975 | 7/1983 | Moore | 206/385 |
| 4,429,793 | 2/1984 | Ehmann | 62/457.2 |
| 4,470,264 | 9/1984 | Morris | 62/457.2 |
| 4,619,678 | 10/1986 | Rubin | 62/457.2 |
| 4,735,318 | 4/1988 | Keffeler | 206/538 |
| 5,181,394 | 1/1993 | Schea, III et al. | 206/570 |
| 5,267,650 | 12/1993 | Gilbilisco | 206/538 |
| 5,318,183 | 6/1994 | Cohen et al. | 206/538 |
| 5,361,603 | 11/1994 | Meritt-Munson | 62/457.2 |
| 5,390,797 | 2/1995 | Smalley et al. | 206/542 |

FOREIGN PATENT DOCUMENTS

| | | |
|---|---|---|
| 0 082 131 | 6/1983 | European Pat. Off. . |
| 1 254 986 | 6/1961 | France . |
| 2 635 580 | 2/1990 | France . |

*Primary Examiner*—William E. Tapolcai
*Attorney, Agent, or Firm*—Flynn, Thiel, Boutell & Tanis, P.C.

[57] ABSTRACT

A portable cold pack for cold storage and transporting of medicinal vials placed on a holder. The cold pack has a hollow, thin-walled housing and a base having a socket depression therein for receiving the holder. The housing and the base define an interior storage space around the holder. The hollow walls of the housing contain therein refreezable liquid for providing cooling energy. The socket depression orients the holder in the storage space in a close relationship to the interior surface of the hollow, thin-walled housing so as to efficiently cool the medicine within the vials. A closure assembly allows repeated access to the holder within the storage space.

8 Claims, 6 Drawing Sheets

COLD PACK FOR VIALS CONTAINING MEDICINE

CROSS-REFERENCE TO RELATED APPLICATION

This application claims the benefit of the following provisional application: U.S. Serial No. 60/026,565, filed Sep. 23, 1996, under 35 USC 119(e)(i).

FIELD OF THE INVENTION

The present invention relates to a portable cold pack for medicinal vials and, more particularly, to a cold pack for use by emergency medical technicians and ambulatory services.

BACKGROUND OF THE INVENTION

Certain medicines are temperature sensitive and must be refrigerated to a lower than room temperature such as insulin. These refrigerated medicines cause particular storage difficulties for emergency medical personnel. Ambulances are equipped with heaters, but they are not commonly equipped with refrigeration units. Medicines requiring refrigeration have heretofore been held in cooling packages and even sometimes placed in conventional coolers (see U.S. Pat. Nos. 5,390,797, 5,390,791, 4,250,998, 4,429,793, 4,368,819, 5,405,012 and 276,590). The energy needed to chill the medicine in the cooling packages and cooler is supplied by a medium such as water, ice, dry ice or a chilled gel. Refrigerating medicines in conventional cooling packages and coolers has many drawbacks, particularly when used with ambulatory services. In general, conventional cooling packages and coolers are bulky and difficult to manipulate. Thus, quick and efficient access to the medicine in the cooling packages and coolers is restricted by the cooling packages and cooler per se. Additionally, the chilling medium may spill.

Ambulances are sometimes too active to return to their base to replenish the supply of refrigerated medicines and/or ice, if and when the medicines approach their upper limit of safe storage temperature. Therefore, the manner in which medicines requiring refrigeration are stored may not chill the medicine for the entire shift of the ambulance operators.

It is therefore an object of the present invention to provide a portable cold pack for refrigerating medicines to hold the medicine below the temperature at which the medicine degrades. Further, it is an object to hold the medicine below the critical temperature for a substantial period of time.

It is further an object of the invention to provide such a cold pack that is easily used in an emergency medical situation, namely, the medicinal vials must be quickly and easily accessible to the medical personnel. The device must also be easily and quickly closed and sealed because time is not only of an essence when accessing the medicine for the patient, but also when it comes time to clean up the treatment site and transport the patient for further medical attention.

It is a further object of the invention to provide such a cold pack which adequately seals itself to preserve the chilled atmosphere within the cold pack for cooling medicines and is easily openable.

SUMMARY OF THE INVENTION

The objects and purposes of the invention, including those set forth above, are met by providing a cold pack for medicinal vials which includes: an outer housing attached to a base, wherein the base has a supporting depression therein for receiving a tray of medicinal vials. The outer housing has a hollow interior for receiving the tray therein. The tray is enclosed by a closure means keeping the tray in a chilled state inside the housing.

To further the cooling ability of the cold pack for medicinal vials, the cold pack may be placed within a reclosable insulated bag. This will further the cooling ability of the cold pack. The insulated bag can be attached to or placed in the drug case used by medical personnel to transport medicines to the patient's location.

BRIEF DESCRIPTION OF THE DRAWINGS

A preferred embodiment of the present invention is described in detail hereinafter with reference to the accompanying drawings, in which.

DETAILED DESCRIPTION

Figure 1:
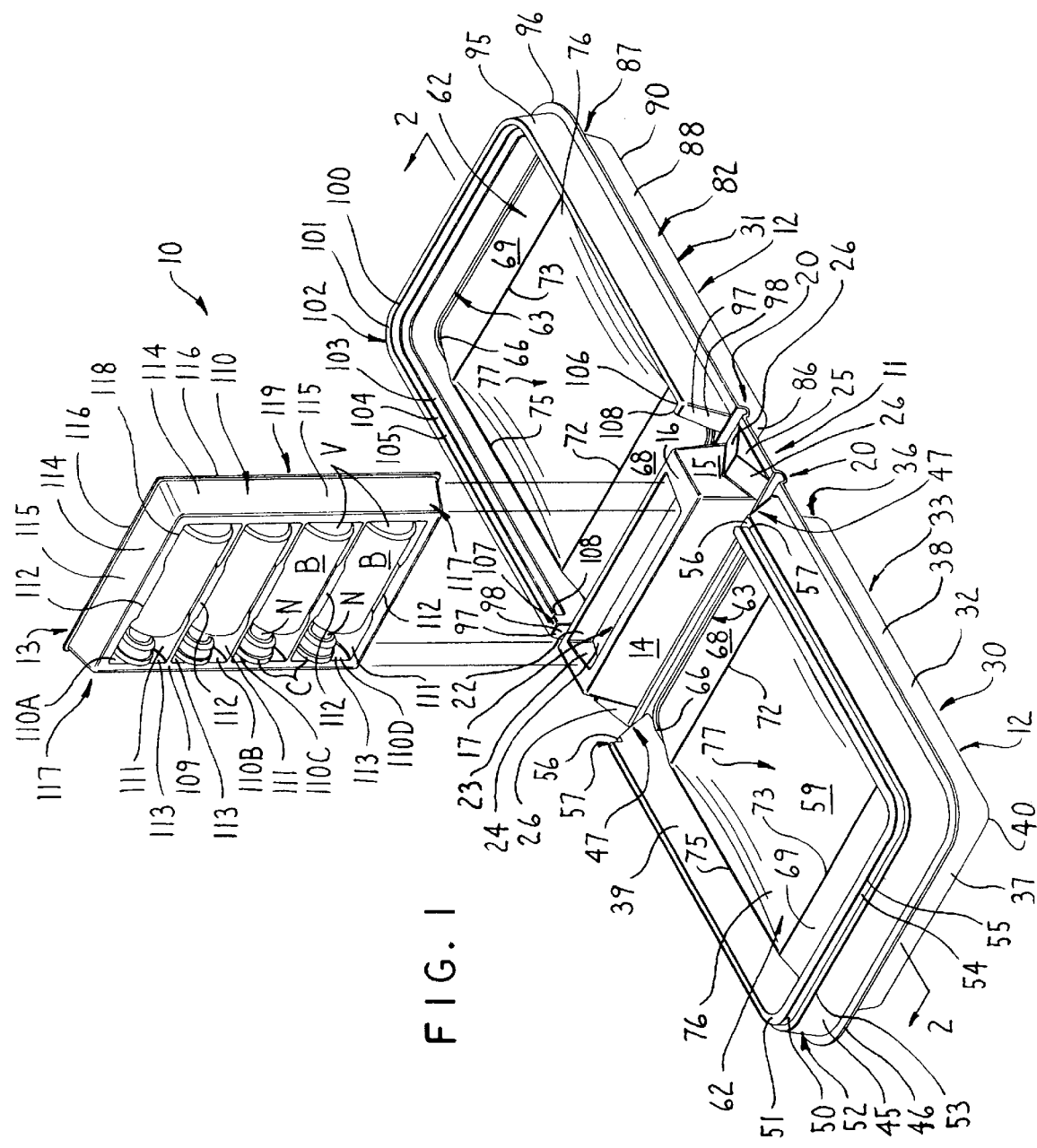
FIG. 1 is an exploded isometric view of the cold pack in an open state.

Certain terminology will be used in the following description for convenience in reference only and will not be limiting. The words "up", "down", "right" and "left" will designate directions in the drawings to which reference is made. The words "in" and "out" will refer to directions toward and away from, respectively, the geometric center of the device and designated parts thereof. Such terminology will include derivatives and words of similar import.

FIG. 1 shows a cold pack 10 which includes a base 11, a hollow, thin-walled housing 12, and a medicinal vial holder 13. All components of the cold pack 10 are made of a uniformly thick thermoplastic material and shaped during a vacuum forming process. The base 11 has a pair of upstanding and upwardly converging side walls 14 and a pair of upstanding and upwardly converging side end walls 15, all contained in respective planes inclined to the vertical. Upper ends of each of the walls 14, 15 terminate in a common plane and are connected by a top wall 16. The top wall 16 has a socket-like depression 17 formed therein which is adapted to removably receive the vial holder 13. A hinge 20 is integrally formed to and extends laterally along a bottom edge of each of the side walls 14.

More specifically, the socket-like depression 17 has opposing side walls 21, 22 and opposing end walls 23 extending between the side walls 21, 22. While the socket-like depression 17 may be of any geometric shape, in the preferred embodiment, the side walls 21 and 22 are generally parallel to each other. Further, one of the side walls 21 is shorter in height than the other side wall 22 so that a bottom wall 24 of the socket-like depression 17 connected to the bottom edge of the side walls 21, 22 is inclined therebetween. The end walls 23 are generally convergingly inclined from the sidewall 22 toward the side wall 21.

The base 11 additionally has a facing member 25 formed on and protrudes outwardly from each of the end walls 15. Each of the facing members 25 has plural facing surfaces 26 thereon angularly related to each other. In this particular embodiment, two angularly related surfaces 26 are provided to form an inverted V-shape in cross section.

Figure 2:
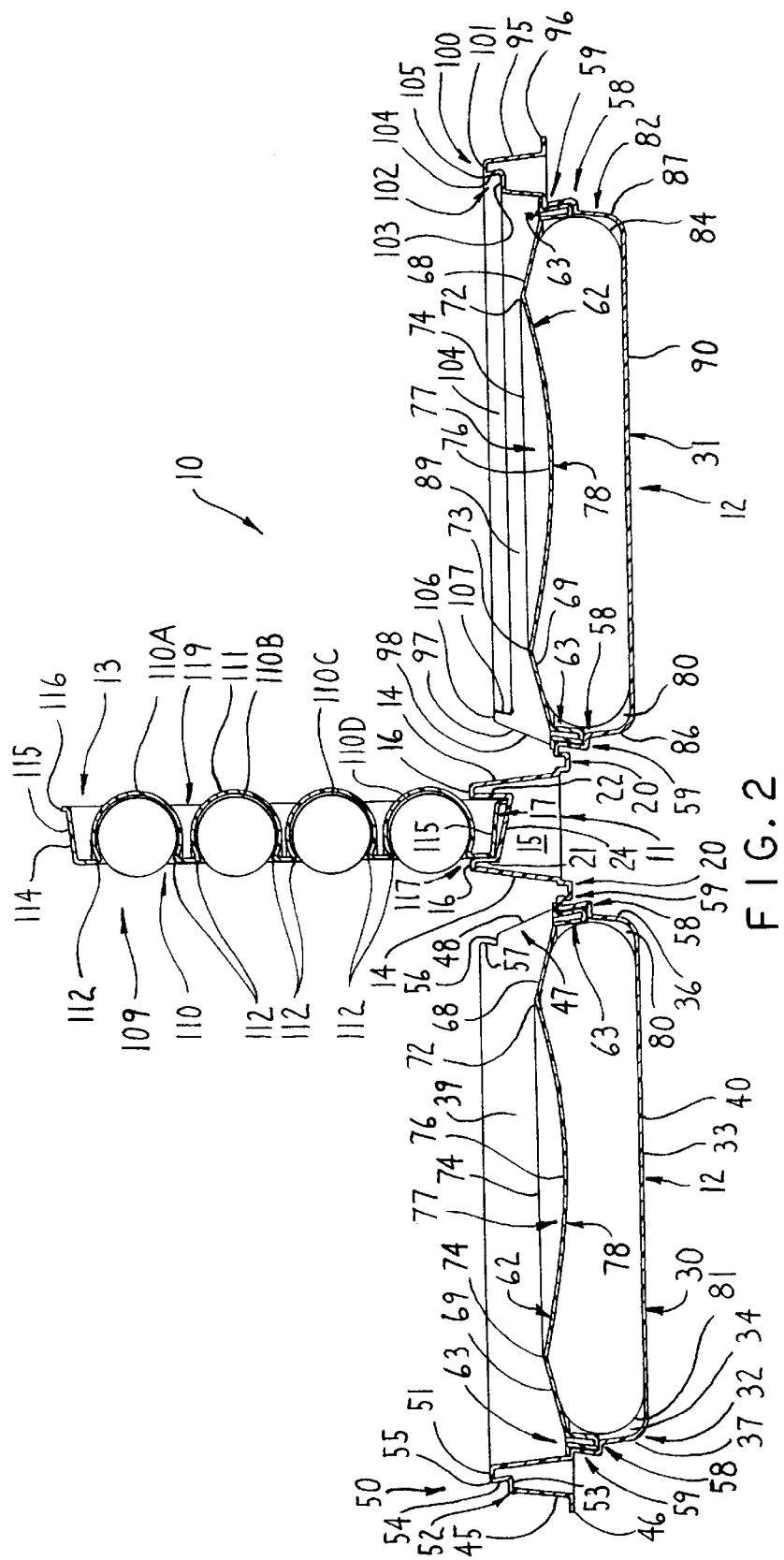
FIG. 2 is a sectional view taken along line 2—2 in FIG. 1 and showing the cold pack in an open state.
Figure 3:
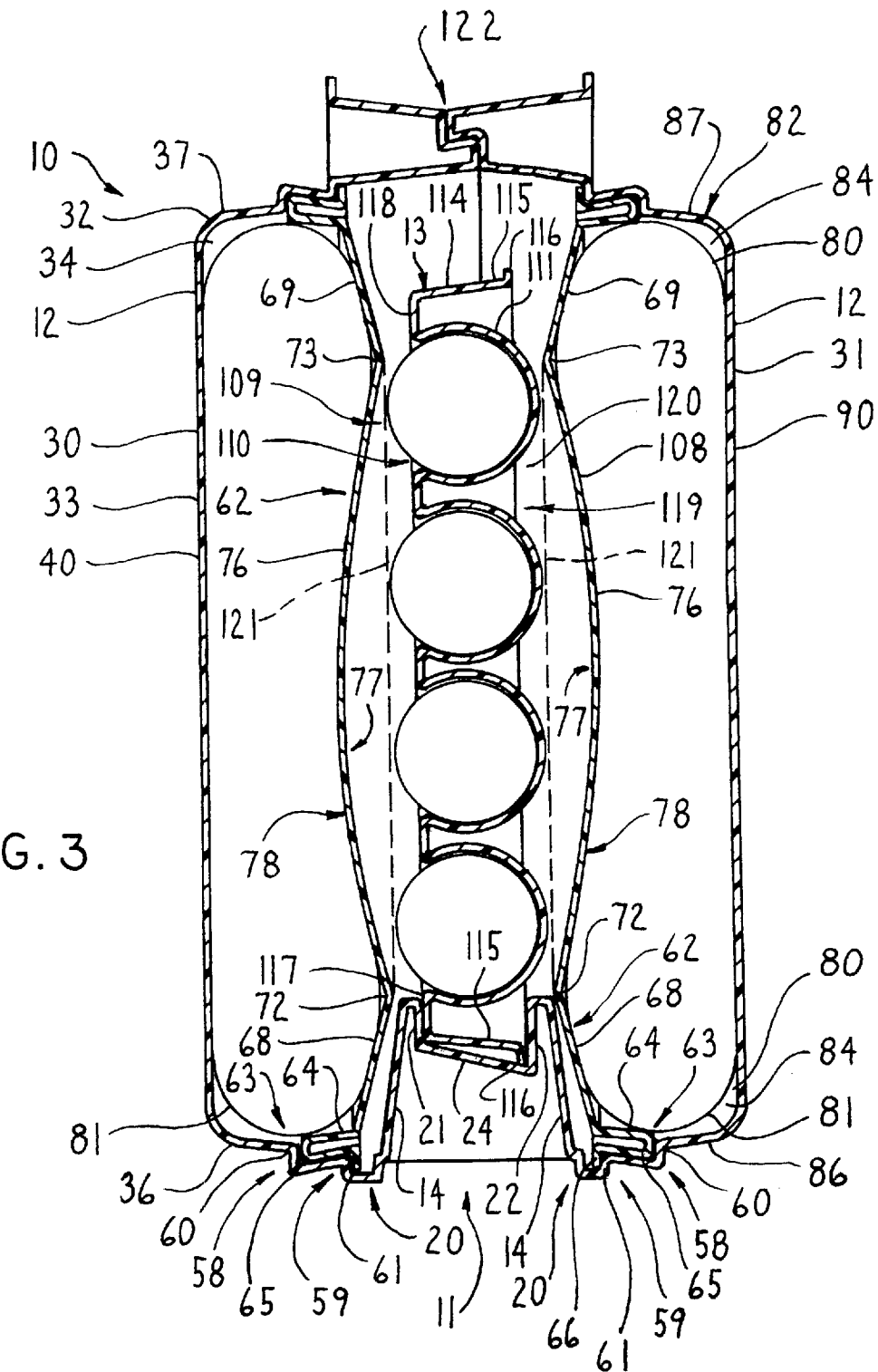
FIG. 3 is a view similar to FIG. 2 and showing with the cold pack in a closed state.

The housing 12, in the preferred embodiment, includes two cover members 30, 31 which are integrally formed with each of the hinges 20, and are each pivotal about the respective hinges between first and second positions. The first position is shown in FIGS. 1 and 2, whereas the second position is shown in FIG. 3. The cover member 30 has a hollow thin walled section 32 defined by a base sheet 33 formed into a generally rectangularly shaped receptacle 34 having upstanding and opposing end walls 36 and 37, as well as upstanding and opposing side walls 38 and 39 connecting the end walls. A bottom wall 40 connects bottom edges of each of the side and end walls 36–39 through correspondingly radiussed corner sections. The hinge 20 interconnects the end wall 36 to the base 11 to facilitate the aforesaid pivotal movement. A skirt 45 projects outwardly from an upper edge of the side and end walls 37–39 and downwardly along an outside facing surface of the side walls 38, 39 and the end wall 37 remote from the hinge 20. A lower outer edge of the skirt 45 forms an outwardly extending flange 46. The upper edge of the side walls 38, 39 and the end wall 37 remote from the hinge 20 are coplanar and terminate a distance above the level of the hinge 20 as shown in FIG. 2. End portions 47 of the side walls 38 and 39 adjacent to and facing the base 11 each define a facing surface 48. Each facing surface 48 is conformed to the respective facing surface 26 on the facing member 25 of the base 11 so that as the cover member 30 pivots about the hinge 20, the opposing facing surfaces 26 and 48 will be in a close juxtaposition to form a loose seal, especially when the cover member 30 is pivoted 90° from the open or first position shown in FIG. 2 to the closed or second position shown in FIG. 3. The angularly related facing surfaces 26 and 48 additionally allow the cover 23 to pivot through the 90° movement without interfering with the structure of the hinge 20.

The juncture between the upper edges of the side walls 38, 39 and the end wall 37 remote from the hinge 20 and the skirt 45 defines a bead or tongue 50 having an uppermost flat surface segment 51 extending parallel to the bottom wall 40 and an acute angle stepped segment 52 forming the upper edge of the skirt 45. A first wall surface 53 of the stepped segment 52 is oriented generally parallel to the flat surface segment 51 and is contiguous with the skirt 45 whereas a second wall surface 54 is inclined to the vertical. The edge joining the inclined wall surface 54 to the flat surface segment 51 defines a lip 55. The region of the cover member 30 generally adjacent and above the level of the hinge 20 is open so that the end portion 47 of the side walls 38, 39 adjacent the hinge 20 straddle about half the left to right dimension of the base 11 illustrated in FIG. 2 when the cover member is moved to the closed position.

The uppermost flat surface 51 terminates shortly before the end portion 47 of the side walls 38, 39 to allow the stepped segment 52 to extend between the flat surface 51 and the end portion 47. The inclined wall surface 54 of the stepped segment 52 has a portion 57 inclined with respect to the vertical extending from a portion 56 of the wall surface 53 to the uppermost flat surface segment 51.

The interior of the rectangularly shapped receptacle 34 includes on the interior walls thereof at about a mid-height level, here on the end walls 36 and 37 and the immediately adjacent area of the contiguous side walls 38 and 39, structure defining spaced lower and upper ledges 58 and 59. Each respective ledge 58 and 59 includes a lower stepped configuration 60 and an upper stepped configuration 61, respectively.

A wall section 62 is received on the ledges 58 and 59 and is cemented in place. The wall section 62 includes a sheet of uniformly thick thermoplastic material having a perimeter thereof formed into a U-shaped flange 63, one leg 64 of the U-shaped flange being contiguous with the sheet. The other leg 65 of the U-shaped flange terminates at an upper edge thereof in an outwardly extending flange 66 adapted to rest on an upper surface area 67 of the upper ledge 59.

The wall section 62 inside the aforesaid perimeter includes a pair of convergingly inclined sections 68 and 69 extending upwardly from opposite ends thereof adjacent the end walls 36 and 37. The wall section 62 also includes a pair of convergingly inclined sections 70 and 71 extending upwardly from opposite sides adjacent the side walls 38 and 39. The pair of convergingly inclined sections 70, 71 generally mirror each other about a center line of the wall section 62. The upper edges 72, 73, 74 and 75 of the four inclined sections 68, 69, 70 and 71, respectively, are coplanar and are contiguous with a wall segment 76 forming generally a centrally disposed depression or pocket 77. The wall segment 76 is in the general form of a segment of a sphere or like surface area. Further, the wall segment 76 is yieldable to forces applied to a bulbous side 78 thereof. In this embodiment, the bulbous side 78 faces and opposes the bottom wall 40 of the rectangularly shaped receptacle 34 in the cover member 30.

A space or cavity 80 is defined between the bulbous side 78 and the bottom wall 40 of the receptacle 34. A bag 81 of refreezable liquid is placed into the cavity 80 and occupies a majority of the space therein. Such bags 81 of refreezable liquid are marketed by Mid-Lands Chemical Company, Inc. of Omaha, Nebr. under the trademark POLAR PACK.

The cover member 31 has a hollow thin walled section 82 defined by the base sheet 33 formed into a generally rectangularly shaped receptacle 84 having upstanding and opposing end walls 86 and 87, as well as upstanding and opposing side walls 88 and 89 connecting the end walls 86, 87. A bottom wall 90 connects the bottom edges of each of the side and end walls 86–89 through correspondingly radiussed corner sections. The hinge 20 interconnects the end wall 86 to the base 11 to facilitate the aforesaid pivotal movement. A skirt 95 projects outwardly from an upper edge of the side and end walls 87–89 and downwardly along an outside facing surface of the side walls 88, 89 and the end wall 87 remote from the hinge 20. The lower outer edge of the skirt 95 forms an outwardly extending flange 96. The upper edge of the side walls 88, 89 and the end wall 87 remote from the hinge 20 are coplanar and terminate a distance above the level of the hinge 20 as shown in FIG. 2. End portions 97 of the side walls 88 and 89 are adjacent to and face the base 11 each defining a facing surface 98.

Each facing surface 98 is conformed to the respective facing surface 26 on the facing member 25 so that as the cover member 31 pivots about hinge 20, the opposing facing surfaces 26 and 98 will be in close juxtaposition to form a loose seal, especially when the cover member 31 is pivoted 90° from the open or first position shown in FIG. 2 to the closed or second position shown in FIG. 3. The seal between the opposed facing surfaces 26 and 98 need not be air tight. It is important, however, that the angularly related surfaces 26 and 98 allow the cover 31 to pivot through the 90° movement without interfering with the structure of the hinge 20.

The juncture between the upper edges of the side walls 88, 89 and the end wall 87 remote from the hinge 20 and the skirt 95 defines a bead or tongue 100 having an uppermost flat surface segment 101 extending parallel to the bottom wall 90 integrally connected to the skirt 95 and an acute angle stepped segment 102 forming the upper portion of side walls 88, 89 and end wall 87. One wall surface 103 of the stepped segment 102 is oriented generally parallel to the flat surface segment 101 and is contiguous with the side walls 88, 89 and end wall 87, whereas the other wall surface 104 is inclined to the vertical. The edge joining the other wall surface 104 to the uppermost flat surface segment 101 defines a lip 105. The region of the cover member 31 generally adjacent to and above the level of the hinge 20 is open so that an end portion 97 of the side walls 88, 89 adjacent the hinge 20 straddle the width of the base 11 when the cover member 31 is moved to the closed position.

The uppermost surface 101 and the stepped segment 102 on both side walls 88 and 89 form a right angle corner as at 106 adjacent the hinge 20. The facing surface 98 extends on those right angle segments between the uppermost flat surface 101 and the hinge 20 as shown in FIG. 1. A portion 107 of the inclined wall surface 104 of the stepped segment 102 extends from the uppermost flat surface 101 to the wall surface 103 and faces the interior of cover member 31.

The interior of the rectangularly shaped receptacle 84 of the cover member 31 is identically shaped to interior of the first described cover member 30. Thus, the same reference numerals have been used to denote the identically formed individual structural features in conjunction with the receptacle 84. Further description of these identically formed features is deemed to be superfluous.

The medicinal vial holder 13 includes a sheet of uniformly thick thermoplastic material formed into a rectangular shaped tray segment 109 having a compartmented depression region 110 thereon. Each compartment 110A, 110B, 110C and 110D of the compartmented region 110 on the tray segment 109 are identical and includes a generally cylindrical bottom wall 111 terminating adjacent the upper edges thereof in integrally formed locking lugs 112 which protrude into the region normally occupied by a medicine containing vial so as to be adapted to yieldingly hold a vial in the compartment. In this embodiment, each lug 112 is smaller in length than a length of the bottom wall 111. End walls 113 are formed at the respective ends of the bottom walls 111. The upper edge of each of the bottom walls 111 and end walls 113 are all coplanar and transition from an uppermost flat surface 118 into a peripherally outwardly extending skirt 114 around the entirety of the holder 13. The skirt 114 includes an inclined wall segment 115 on each of the four sides of the rectangle and which are joined together at each of the four corners. The lower edge of the skirt 114 is formed into an outwardly extending stiffening flange 116. The structure of the skirts 114 on each of the long sides and narrow sides is elastically yieldable.

Either of the narrow ends of the tray segment 109 is designatable as a holder segment 117 conforming in shape to the shape of the socket-like depression 17 on the base 11. That is, the outward inclination of the wall segment 115 at the narrow end is generally similarly inclined to the bottom wall 24 of the socket-like depression 17. Further, the spacing between the coplanar surface 118 extending between the upper edges of the skirts 114 and the upper edges of the bottom walls 111 and an opposite facing surface 119 on a side of the flange 116 remote from the surface 118 is nearly equal to the spacing between the side walls 21 and 22 of the socket-like depression 17. Further, the wall segments 115 of the skirt 114 on opposite sides of the long sides of the tray segment 109 are inclined at an angle that is generally parallel to the end walls 23 of the socket-like depression 17 when a longitudinal axis of the holder 13 is oriented perpendicular to the top wall 16 of the base member 11. As a result, a narrow end of the tray segment 109, namely, the holder segment 117 thereof is receivable in the socket-like depression 17 as shown in the drawings. The fit between the holder segment 117 and the walls 21–24 of the socket-like depression 17 is snug.

In use the holder 13 is received by the socket-like depression 17. The flange 116 on the long side side wall portions of the wall segment 115 of the holder 13 is slightly wider than the spacing between the end walls 23 of the socket-like depression 17. Thus a slight application of force is applied to the holder 13 to deform the elastically yieldable wall segments 115 of the long side skirts 114 due to the long side flanges 116 contacting the end walls 23 of the socket-like depression 17. Once the holder 13 is in the depression 17, the elastically yieldable wall segments 115 continue to press outwardly onto the end walls 23 to maintain the contact between the flanges 116 at the end thereof against the end walls 23 to thereby enhance the snug fit of the holder 13 in the depression 17 in the base 11.

When the holder 13 is to be removed from the depression 17, it may be pulled upwardly out of the depression 17. Alternatively, and if the holder 13 is held quite firmly in the depression 17, it may be necessary for a person (user) to pivot the holder 13 by gripping the holder above the holder segment 117 positioned in the depression 17 urging the exposed tray segment 109 of the holder 13 clockwise as shown in FIG. 2 about a pivot axis defined by the juncture between the surface 119 of the flange 116 and the upper edge segment of the side wall 22 of the depression 17 so as to easily overcome the snug fit and, facilitate removal of the holder 13 from the depression 17.

Figure 4:
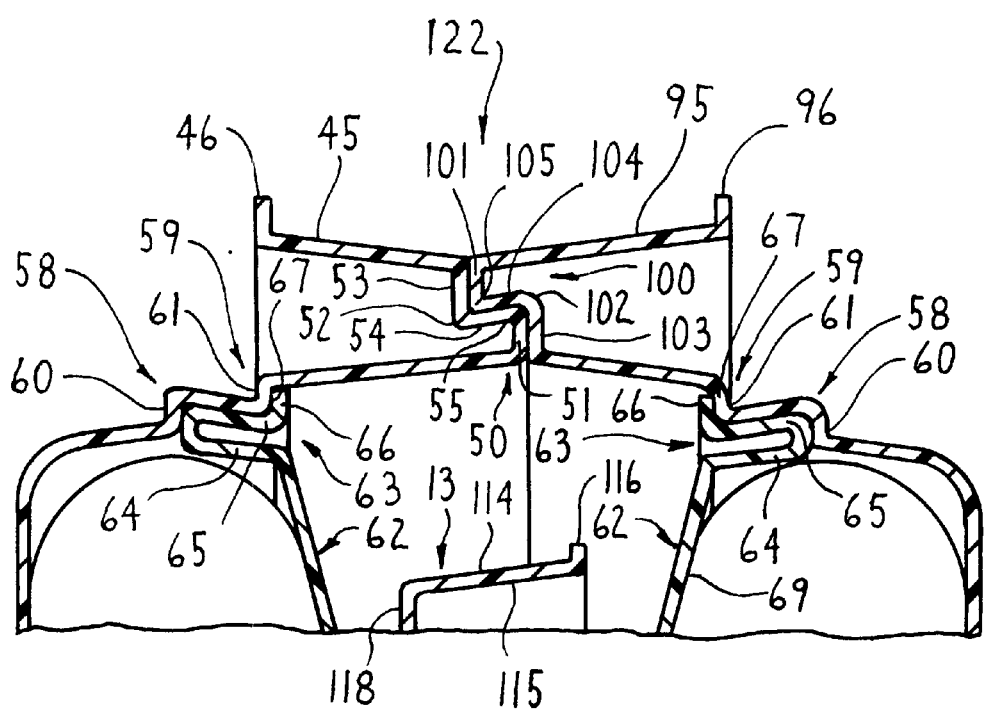
FIG. 4 is an enlarged view of the top area of FIG. 3.
Figure 5:
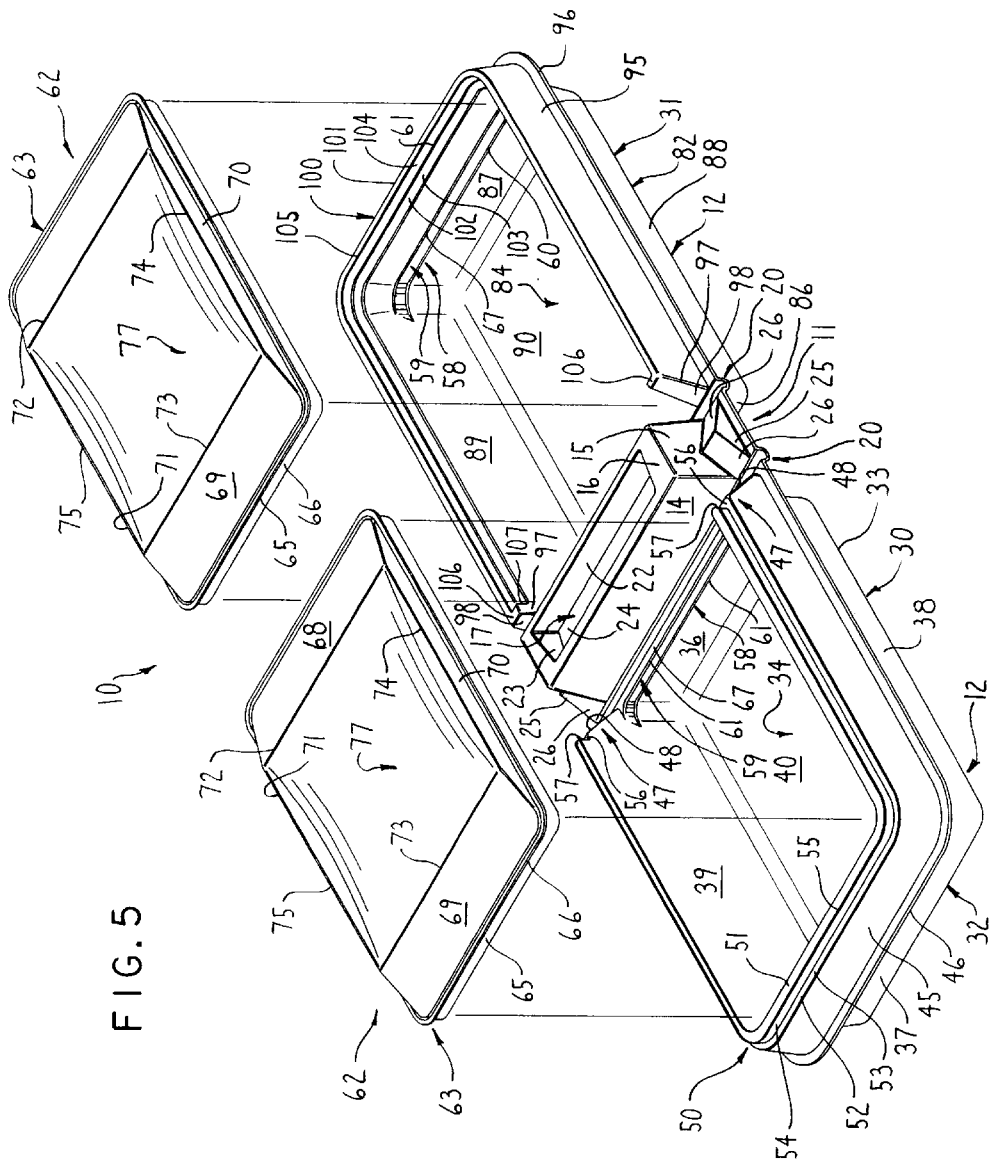
FIG. 5 is an exploded view similar to FIG. 1.

As shown in FIGS. 3 and 4, the lips 55 and 105 and associated stepped segments 52 and 102 are nested with one another to form a clasp 122 holding the cover members 30 and 31 in the closed position. The surfaces 51 and 101 face one another when the cover 30 and 31 are in the closed position.

The differing depths of the side walls 21, 22 of depression 17 allows the easy removal of the holder 13 from the depression 17 by pivoting the holder clockwise toward the cover member 31. The shorter depth of the side wall 21 allows the coplanar surface 118 of the holder segment 117 to be easily removed from the depression 17 during the clockwise movement. On the other hand, the side wall 22 has a depth into the depression greater than side wall 21 which prevents the holder 13 from pivoting counterclockwise toward the cover member 30. Thus, when an emergency medical technician removes the holder 13 from the depression 17, the holder 13 is pivoted clockwise so that the medicine containing vials will face upwardly toward the emergency medical technician and to provide ready access to the vials.

When transitioning the cold pack 10 from the closed position to the open position, the user can grasp the flanges 46, 96 and/or the skirts 45, 95 to apply opposing separating forces to each cover member 30, 31. The flexibility of the thermoplastic construction allows the lips 55, 105 to thereby be forced past each other and the open position is attained by rotating the cover members 90° in respective directions away from the holder 13. The cold pack 10 may also be opened by placing the cold pack on the bottom wall 40 of the cover member 30, then rotating cover member 31 through 180° so as to lie in the same plane as the cover member 31. The holder 13 in the depression 17 will resist falling out of the depression 17 due to the aforesaid snug fit in the depression.

Figure 6:
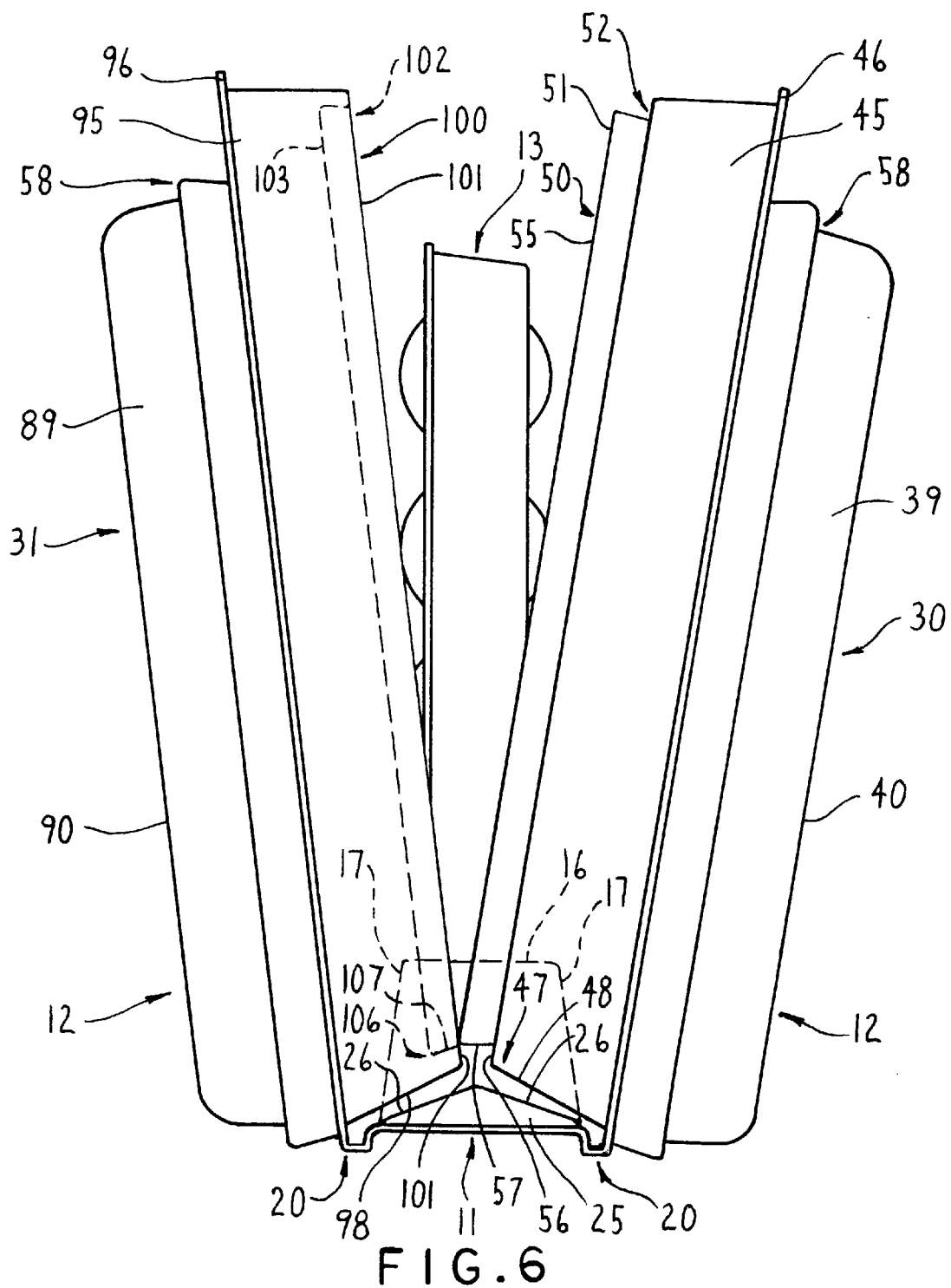
FIG. 6 is an enlarged partial view of the cold pack transitioning between a closed position to an open position or vice versa.

As mentioned above, to transition the cold pack 10 from its open or first position to its closed or second position, the cover members 30, 31 are rotated 90° about the hinges 20 toward the holder 13. Just prior to attaining the second or closed position (FIG. 6), the portions 57 of the inclined wall surface 54 slidingly engage the portions 107 of inclined wall segment 104 of each of the right angle corner segments 106. The sliding engagement of the portion 57 and the wall segment 107 effects an alignment of the lips 55 and 105 to facilitate them snapping past each other locking the cold pack 10 into the closed or second position. When the cold pack 10 is in the closed position, the portion 56 of the surface 53 faces and opposes the right angled portion of the flat surface segment 101.

When the cold pack 10 is in the closed position, a storage space 120 is defined by and between the interior surfaces of the side walls 38, 39, 88, 89 above (FIG. 2) the wall sections 62 and the interior surfaces of the end walls 37, 87 for cold storing the holder 13 positioned in the socket-like depression 17. The storage space 120 is essentially insulated from the outside environment and stores the temperature sensitive medicine below its critical temperature for a substantial period of time.

The cold pack 10 can be reused by placing the entire cold pack 10 in a freezer and refreezing the liquid in the bags 81 positioned therein. The use of the ice packs or bags 81 to provide the coolant has a serious drawback, namely, the ice bags expand when frozen. The depression or pocket 77 formed by the wall segment 76 will yield to the expanding ice bag during the freezing thereof. The wall segment 76 will expand to the broken line showing at 121 in FIG. 3 and to a close juxtaposition to the medicine containing vials on one side of the holder 13 and the surface 119 on the other side of the holder 13.

The medicinal vials V are of a commonly used shape having a cylindrical liquid containing main body B with a reduced diameter neck N extending from one end of the body. A cap C is positioned on an end of the neck remote from the body for sealing the liquid medicine within the vial.

Although a particular preferred embodiment of the invention has been disclosed in detail for illustrative purposes, it will be recognized that variations or modifications of the disclosed apparatus, including the rearrangement of parts or altering the number and size of compartments in the holder, lie within the scope of the present invention.

The embodiments of the invention in which an exclusive property or privilege is claimed are defined as follows:

1. A portable package for cold storing and transporting medicine stored in vials, comprising:

a holder means for holding at least one vial thereon;

a housing having a base and a hollow, thin-walled wall construction, said hollow wall construction defining first and second cover members each hingedly secured to said base at spaced and parallel extending locations thereon to orient said base intermediately therebetween, said first and second cover members each being pivotable about respective axes of the hinged securement thereof to said base and thence being movable with respect to said base between a first position whereat each said cover member exposes a surface area forming a depression opening outwardly in a common first direction, and a second position whereat peripheral edges of said cover members tightly engage one another and the respective depressions face one another to define a storage space, said hollow wall construction defining a refreezable liquid receiving cavity therein, said cavity having a refreezable liquid therein, said base having a support means thereon for fixedly and removably supporting said holder means in said storage space and in close juxtaposition to said surface area forming said depressions; and closure means for providing access to and removal of said holder means from said storage space.

2. The portable package for cold storing and transporting medicine stored in vials according to claim 1, wherein said closure means is defined by a locking tongue and groove means on said peripheral edges for latching said cover members together to securely enclose said holder means within said storage space.

3. The portable package for cold storing and transporting medicine stored in vials according to claim 2, wherein a segment of the hollow wall construction defining said surface area and forming the depression on each cover member has a yieldable characteristic in response to a freezing of said refreezable liquid and a resulting expansion of volume occupied by the frozen liquid to cause the surface area to become oriented closer to said holder means than when said liquid is in the liquid state.

4. The portable package for cold storing and transporting medicine stored in vials according to claim 3, wherein at least one vial is oriented in said depression, a peripheral surface of said vial being spaced from each said surface area a sufficient distance to facilitate a yielding of said surface area in response to an expansion of the volume of space occupied by said liquid transitioned to a frozen state and still facilitate engagement of said peripheral edges of said closure members when in said second position.

5. The portable package for cold storing and transporting medicine stored in vials according to claim 2, wherein said support means on said base includes a socket depression opening outwardly, when said cover members are in said first position, in said common direction, said holder means including a shaped segment conforming to and being removably received in said socket depression as well as a tray segment contiguous with said shaped segment, said tray segment having a compartmented depression thereon for medicinal vials therein, and opening outwardly in a second direction perpendicularly to said first direction, said tray segment being fully housed in said storage space when said cover members are in said second position.

6. The portable package for cold storing and transporting medicine stored in vials according to claim 5, wherein said tray segment is contained in a plane which extends generally transversely to said cover members when said cover members are in said first position and lie in a common plane.

7. The portable package for cold storing and transporting medicine stored in vials according to claim 5, wherein said compartmented depression includes plural parallel separation walls and locking rib means for facilitating a holding of multiple vials between mutually adjacent pairs of said separation walls and for limiting relative motion and contact between vials oriented between respective pairs of said separation walls.

8. The portable package for cold storing and transporting medicine stored in vials according to claim 1, wherein at least one of said cover members includes a flange integrally extending from an exterior of said at least one cover member to allow a user of the portable package to readily grip said flange to effect an opening of said closure means to said second position so as to allow access to said holder means.

* * * * *